(12) United States Patent  
Houard et al.

(10) Patent No.: US 8,506,595 B2  
(45) Date of Patent: Aug. 13, 2013

(54) ANCHORING AND FIXING IMPLANT AND SURGICAL ASSEMBLY FOR ITS IMPLANTATION

(75) Inventors: William Houard, Labastide-Rouairoux (FR); Eric Bautrant, Puyricard (FR); Fabrice Fonseca, Cuges les Pins (FR); Philippe Berret, St Paulet Valmalle (FR)

(73) Assignee: Textile Hi-Tec (T.H.T.), Verreries de Moussans (FR)

( * ) Notice: Subject to any disclaimer, the term of this patent is extended or adjusted under 35 U.S.C. 154(b) by 174 days.

(21) Appl. No.: 12/443,945

(22) PCT Filed: Oct. 3, 2007

(86) PCT No.: PCT/FR2007/052067  
§ 371 (c)(1),  
(2), (4) Date: May 7, 2009

(87) PCT Pub. No.: WO2008/040914  
PCT Pub. Date: Apr. 10, 2008

(65) Prior Publication Data  
US 2010/0016894 A1   Jan. 21, 2010

(51) Int. Cl.  
*A61B 17/04* (2006.01)

(52) U.S. Cl.  
USPC ................................................. 606/232

(58) Field of Classification Search  
USPC ................... 606/75, 151, 157, 158, 232, 221; 411/457, 458, 459; 24/296, 626, 710.8, 710.9, 24/711.1  
See application file for complete search history.

(56) References Cited

U.S. PATENT DOCUMENTS

| 625,062 | A | * | 5/1899 | Roberts | ........................ 24/710.8 |
| 5,030,224 | A | | 7/1991 | Wright | |
| 5,203,787 | A | | 4/1993 | Noblitt | |
| 5,411,522 | A | * | 5/1995 | Trott | ............................ 606/232 |
| 5,501,683 | A | | 3/1996 | Trott | |
| 5,573,543 | A | | 11/1996 | Akopov | |
| 6,174,323 | B1 | | 1/2001 | Biggs | |
| 6,722,050 | B2 | * | 4/2004 | Winton, III | ..................... 33/534 |
| 2004/0078054 | A1 | * | 4/2004 | Biggs et al. | ................... 606/232 |

FOREIGN PATENT DOCUMENTS  
WO   WO 2005/041784 A1   5/2005

* cited by examiner

*Primary Examiner* — Thomas McEvoy  
(74) *Attorney, Agent, or Firm* — Kenyon & Kenyon LLP

(57) ABSTRACT

The anchoring and fixing implant is constituted by a continuous wire with rectilinear portions and curved portions. It comprises: a) a central curved portion forming a winding of substantially 1.5n turns, n being, for example, equal to 1, b) on either side and in extension of said central portion, a set of two rectilinear portions, specifically an intermediate portion and an end portion, connected to one another by a bent portion at an angle of the order of 30° to 90°. Also, the rectilinear end portions are oriented divergently so as to make an angle of the order of 60° to 180° between them. The surgical assembly comprises an implant as above, a fixing thread intended to be threaded in the central curved portion of the implant and an ancillary device.

3 Claims, 3 Drawing Sheets

ANCHORING AND FIXING IMPLANT AND SURGICAL ASSEMBLY FOR ITS IMPLANTATION

This is a 371 national phase application of PCT/FR2007/052067 filed 3 Oct. 2007, which claims priority to French Patent Application No. 06/08703 filed 4 Oct. 2006, the contents of which are incorporated herein by reference.

FIELD OF THE INVENTION

The present invention relates to the field of surgical implants. It concerns more particularly an implant for executing anchoring and fixing, or even tensioning, other implants, especially slit-film yarns or prosthetic plates in tissue, this fixing and this tensioning being carried out using at least one suture thread.

BACKGROUND OF THE INVENTION

Using anchoring and fixing implants is a highly current practice when the surgeon has to permanently install a prosthetic plate or a slit-film yarn, without the risk of it migrating. Such an implant must fulfill two functions. It must first allow passage, sliding and blockage of the suture thread. This first function is generally fulfilled by the presence in the implant of an opening in which the suture thread can be threaded, without the risk of it slipping out during handling by the practitioner. The second function is the anchoring capacity, that is, blockage in position in the tissue. Such an anchoring and fixing implant must also be smaller in size so that its presence does not constitute a constraint as such. A large number of different anchoring and fixing implant models, some of which are constituted by a continuous thread with rectilinear portions serving to fulfill the function of anchoring and recurved portions serving especially to form an opening serving the function of fixing the thread by folding, has already been put on the market.

In the document WO 2005/041784 A1, the implant which is illustrated in FIG. 1, comprises a recurved portion substantially making up three quarters of a circle prolonged by two rectilinear portions crossing at a right angle and terminating in pointed ends.

In the document U.S. Pat. No. 5,203,787, the implant comprises a central recurved portion forming a complete circle, and two rectilinear portions, opposite one another and ending in threaded ends.

In these two embodiments, the opening for the passage of the suture thread is constituted by the recurved portion in an arc of a circle, where the practitioner is not strictly obliged to thread the suture thread through the opening as in the case of a needle but where he can introduce it by sliding part of this thread between the two rectilinear portions until it enters the opening. But there is a risk that during manipulation and the operation the thread disconnects from the implant by exiting from the recurved portion via the same path it took when being introduced. To avoid this risk, document WO 2005/041784 provides a blockage system of the two rectilinear portions in their superposed state, though this solution makes manufacturing of the implant complex.

The implant described in document U.S. Pat. No. 5,501,683 comprises three bent portions, each describing an arc of a circle of 180°, specifically a median portion and two side portions, opposite but slightly offset. The rectilinear portions which are in the extension of said bent portions are therefore all parallel to one another. The rectilinear portions of the median portion rejoin the internal rectilinear portions of the two side portions by forming folds at 45°, which interleave in one another. These are the two external rectilinear side portions which act as anchoring of the implant in the tissue. For this to happen, it is necessary to employ an ancillary which on the one hand is capable of introducing the implant in its resting configuration, with the two external rectilinear side portions parallel to one another and which on the other hand and above all is capable of spreading apart said two external side portions so as to move them away from each other, thus executing penetration of their ends into the tissue, on either side of the previously bored implantation hole. As for the suture thread, it is introduced not into the opening formed by the recurved median portion but into the U-shaped part delimited between the two external side rectilinear portions. In this document U.S. Pat. No. 5,501,683 the opening formed by the recurved median portion acts as prehension of the implant by a mobile piece of the ancillary, enabling translation towards the rear of said implant, whereas the external rectilinear side portions come to be supported against an oblique surface, thus creating desired spread.

In the document U.S. Pat. No. 6,174,323, the implant comprises a central recurved portion in a semi-circle. Blocking means, for example a staple, is necessary to ensure blockage of the two yarns of the suture thread upstream of the implant (designated 50 in FIG. 16) and thus to prevent the suture thread from disconnecting from the implant.

SUMMARY OF THE INVENTION

The aim of the present invention is to propose an anchoring and traction implant which can easily be made and assembled relative to that described in the document U.S. Pat. No. 5,501,683 and which eliminates the disadvantages of the implants proposed in the documents WO2005/041784, U.S. Pat. Nos. 5,203,787 and 6,174,323.

It relates to an anchoring and fixing implant which is constituted by a continuous thread with rectilinear portions and recurved portions.

Characteristically, this implant comprises:
a) a central recurved portion forming a sealing winding of at least substantially 1.5 turns,
b) on either side and in extension of said central portion a set of two rectilinear portions, specifically an intermediate portion and an end portion which are connected to one another by a bent portion at an angle of the order of 30 to 90°.

Also, the rectilinear end portions are oriented divergently so as to create between them an angle of the order of 60 to 180°.

In a variant embodiment the sealing winding of the central recurved portion substantially forms one and a half turns. This particular arrangement allows simplification of manufacturing and a reduction in bulk of the implant. It can likewise allow the introduction of the suture thread by having it slide between the two rectilinear portions and slide along a one and a half turns until it enters the central orifice of said turn. The fact that this is one and a half turns and no longer a recurved portion in an arc of a circle describing at most 180° prevents the suture thread from involuntarily slipping out of this opening.

The continuous thread is preferably made of shape-memory material which allows the recurved portions to act as articulations, such that, in a position of introduction the two rectilinear end portions can be stressed towards one another so as to form an angle of the order of 10 to 30° between them and, in an implantation position, resume the initial angular position of the order of 60 to 180°.

According to a variant embodiment, the length of the rectilinear end portions is less than the length of the intermediate rectilinear portions. As will be better understood from the following description of an example of an ancillary implantation, this arrangement effectively anchors the implant in the tissue due to the deployment of the two end portions, while partially keeping the implant in a longitudinal direction inside the ancillary, before it is fully released.

According to a variant embodiment, the intermediate rectilinear portions make an angle of the order of 10 to 30° between them. In this case, the centres of the three recurved portions are preferably in the same plane. It is this configuration which is preferred and will be described hereinbelow.

The object of the present invention is also a surgical assembly which comprises:
- an anchoring and fixing implant exhibiting all or part of the above characteristics,
- a fixing thread intended to be threaded in the central recurved portion of the implant,
- un ancillary de pose in the form of a hollow tube comprising an open cavity at its distal end, for acting as housing for the implant in a position of introduction in which it has its central recurved portion in the bottom of the cavity, and its rectilinear end portions which are stressed towards one another supported on the side wall of said cavity.

To evacuate the implant from the cavity all the operator needs to do is hold the fixing thread to make the central recurved portion rise and make the rectilinear end portions leave the cavity.

In the surgical assembly for placing a surgical instrument, especially a slit-film yarn or prosthetic plate, with two anchoring and fixing implants and two fixing threads each threaded into the central recurved portion of an implant, at least one fixing thread preferably has a first yarn not fixed to said instrument, which forms a sliding knot around the second yarn fixed to said instrument, for realizing the tensioning of the instrument between the two implants.

BRIEF DESCRIPTION OF THE DRAWINGS

The present invention will be better understood from the following description of a preferred embodiment of an anchoring and fixing implant, illustrated by the attached diagram, in which.

DETAILED DESCRIPTION

The function of the implant 1 is to ensure anchoring in tissue, especially osseous tissue, of another implant such as a slit-film yarn or prosthetic plate, by means of a linking thread, or suture thread. The implant 1 is formed from a rigid continuous thread of circular cross-section, for example around 0.5 mm in diameter, or polygonal. This thread is made from a stable and bio-inert material, for example a metal alloy, especially an alloy of titanium, stainless steel or nickel titanium alloy. It can also be made of a resorbable material, for example from polymer of natural or synthetic origin including polylactide, polyglycolid, poly-ϵ-caprolactone, polyhydroxy butyrate, polyhydroxy valerate, polycarbonates and the like, cellulose, polysaccharides, starch, their homopolymers, their copolymers and their derivatives.

In the case of resorbable materials, it is preferable for the mechanical properties, in terms of rupture force of the implant, to evolve under the following conditions, specifically on completion of a period of six months after the implantation loss of the order of 50% of the initial properties and after a loss of 100% of the initial properties.

Figure 1:
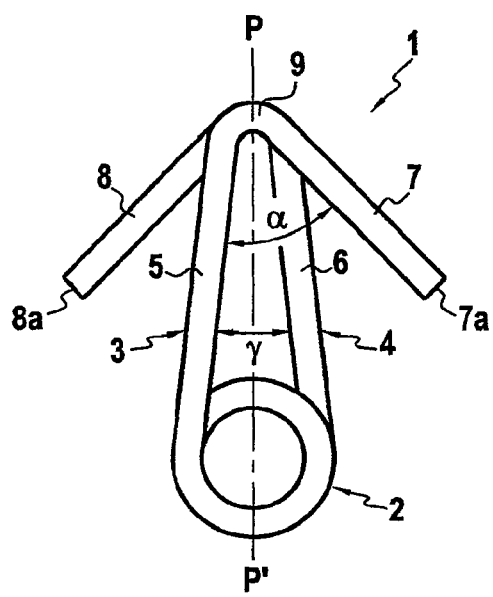
FIG. 1 is a schematic side elevation of said implant.

The rigid continuous thread in question complies with an automatic specialized material for taking the form such as illustrated in FIG. 1, which corresponds to continuous chaining of rectilinear segments and recurved portions.

Figure 2:
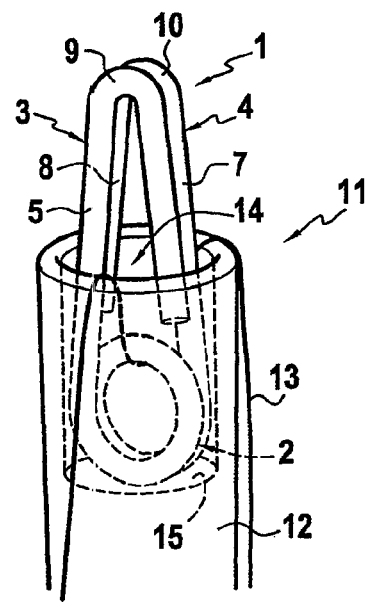
FIGS. 2, 3 and 4 are schematic perspective illustrations of the implant of FIG. 1 and of its ancillary de pose, in a position of introduction (FIG. 2), in an intermediate evacuation position (FIG. 3) and in an implantation position (FIG. 4)
Figure 3:
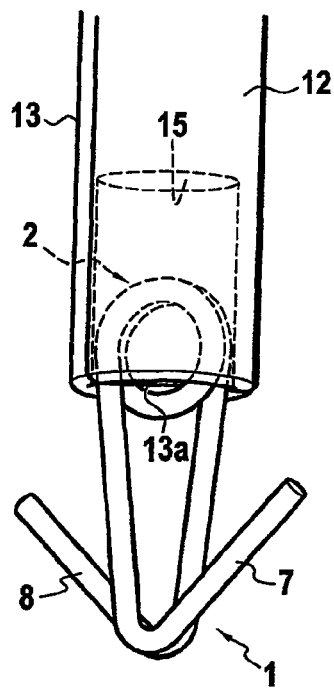
Figure 4:
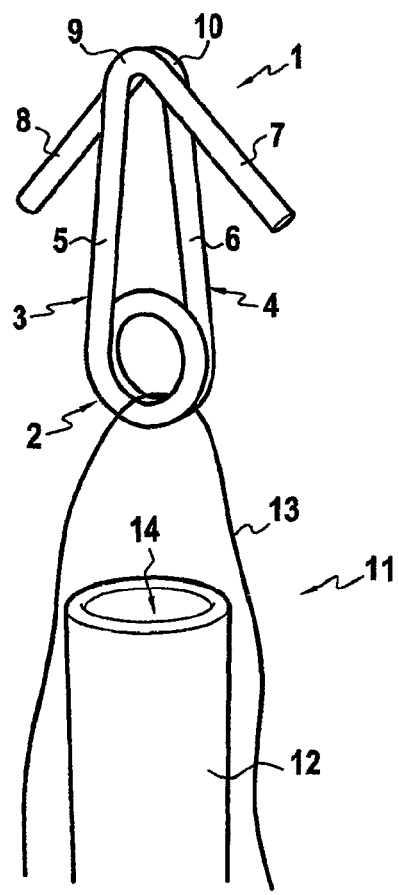

More precisely the implant 1 comprises:
a) a central portion 2 recurved so as to form a sealing winding constituted substantially by at least 1.5 turns. The number of turns is not visible in FIG. 1, in side elevation, but it appears clearly in FIGS. 2 to 4, given that in the illustrated example the recurved central portion 2 substantially comprises only one and a half turn;
b) on either side and in extension of said central portion 2 a set of two rectilinear portions 3,4, specifically an intermediate end segment 5, 6 and an end segment 7, 8, which, in each set are connected to one another by a bent portion 9, 10, said bend describing an angle α of the order of 30 to 90°.

Also, the two end segments 7, 8 are oriented divergently so as to make an angle β of the order of 60 to 180° between them.

If the given curve at the central portion 2 strictly made 1.5 turns, the two intermediate segments 5, 6 would be strictly parallel. Such is not the case in the illustrated example for which this winding is slightly greater than one and a half turns such that the two intermediate segments 5, 6 form between them an angle γ of the order of 10 to 30°. Also, the curve centres of the three recurved portions 2, 9, 10 are in the same plane PP', which results in the implant 1 having a particularly compact structure and a perfectly symmetrical behaviour.

The presence of the three curve centres in the same plane could be attained with a central portion 2 strictly forming 1.5 turns, but in this case it would be necessary to increase the radius of curve of the bent portions 9, 10.

The length L0 of the end segments 7, 8 is less than the length L1 of the intermediate segments 5, 6. This arrangement is not strictly obligatory but does prevent said end segments 7, 8 from being supported on the central recurved portion 2 in the folded introduction state, which could increase the bulk of the implant and thus require an implantation hole of larger diameter to be bored in the tissue.

The ends 7a, 8a of the end segments 7, 8 could optionally be threaded but it is deemed preferable that they are not traumatic for the tissue. Due to this they are exempt from sharp edges, as their edges are slightly rounded.

In a precise embodiment, given by way of inexhaustive example, the implant 1 is made from a rigid thread having a diameter of the order of 0.5 mm. Its total length, according to the plane PP' is of the order of 8 mm. The external diameter of the central recurved part is of the order of 3 mm. The length L0 of the two end segments 7, 8 is of the order of 4 mm. The angle α is of the order of 50°, the angle β is of the order of 90° and the angle γ is of the order of 15°.

When the implant 1 is in a rest position, the distance separating the external edges from the ends 7a, 8a of the end segments 7, 8 is of the order of 7 mm.

An ancillary 12 of particularly simplified design is provided for placing the implant 1 since it comprises a simple cylindrical tube having a distal cavity 14.

The surgical assembly 11 which is proposed to the operator is preferably disposable, in sterile packaging, this assembly comprising the anchoring and fixing implant 1, in a folded position, lodged inside the ancillary 12, with the fixing thread 13 previously threaded through the central recurved portion 2 of the implant 1.

In this surgical assembly 11, the implant 1 is lodged in the open distal cavity 14, at the bottom 15 of which the central recurved portion 2 is placed.

The diameter of this cavity 14 is slightly larger than the external diameter of the central recurved portion 2.

For placing the implant 1 in the cavity 14, a compression action of the two end segments 7, 8 is executed so as to move them closer to one another, by reducing the angle β to a value which is close to that of the angle γ such that the spread of the end edges 7a, 8a of said segments 7, 8 is equivalent to the external diameter of the central part 2. The implant 1, at least partially including the end segments 7, 8, can be introduced to the cavity 14 in this way.

FIG. 2 illustrates the implant 1 lodged partially inside the cavity 14, with the two end segments 7, 8 folded, the ends 7a, 8a of the two said segments coming into contact with the inner wall of the cavity 14. It is clear that it is the bent portions 9, 10 which play the role of hinges to create angular reduction between the intermediate segments 5, 6 and the end segments 7, 8.

Once the implant 1 is introduced inside the ancillary, the end segments 7, 8 tend naturally to return to their initial angular position and are prevented from doing this by the inner wall of the cavity. The application force which is thus exerted by these segments ensures that the tie 1 is held inside the ancillary 12, irrespective of the positioning of the latter.

To implant the implant 1, the practitioner first bores a hole in the tissue. This hole is generally the same external diameter of the distal part of the ancillary 12 so that said distal part including the implant 1 can penetrate. It exerts traction on the two yarns of the fixing thread, exceeding the ancillary 12, which tenses the portion 13a of the thread which was inside the cavity 14, as illustrated in FIG. 3, makes the central recurved portion 2 rise and makes the end portions 7, 8 leave the cavity 14.

FIG. 3 illustrates the moment when the implant 1 is solid with the ancillary 12 by its central recurved portion but when the two end segments 7, 8, released from the constraint of the inner wall of the cavity 14 have returned to their initial angular position of angle α and have penetrated the tissue, somehow forming two harpoon hooks.

FIG. 4 illustrates the final step where the implant 1 is anchored in the tissue, the practitioner withdraws the ancillary 12 and can utilize the fixing thread 13 for creating definitive fixing of the other implant by making use of this anchoring implant 1.

The implant 1 and its pose ancillary 12 are intended for surgery, whether this is orthopaedic, digestive, urological or even gynaecological surgery and whether arthroscopic or conventional.

Figure 5:
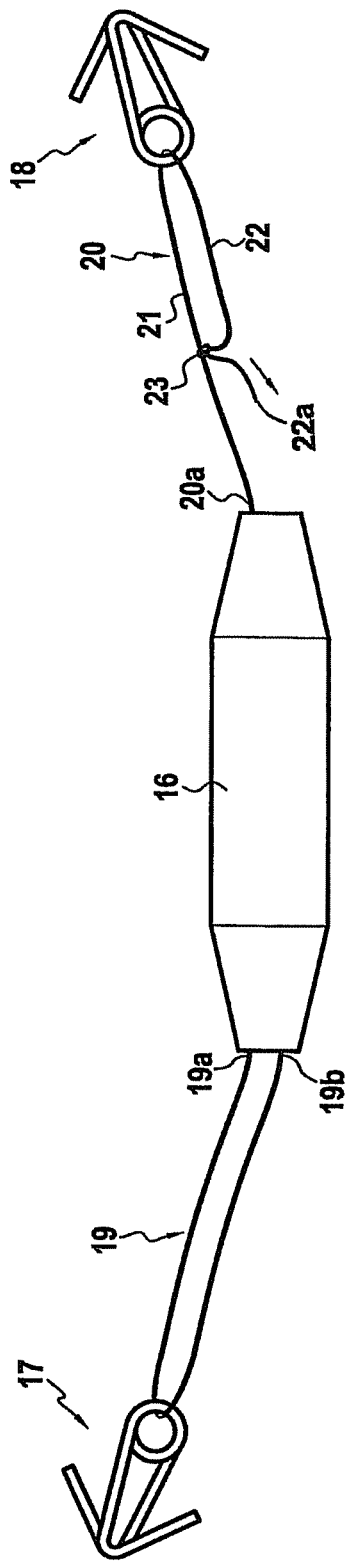
FIGS. 5 and 6 are schematic illustrations of two examples of placing slit-film yarn using two implants.

FIG. 5 schematically illustrates placing a slit-film yarn 16 by means of two anchoring and fixing implants 17, 18 and two fixing threads 19, 20. The two implants 17, 18 have been successively implanted into the tissue at appropriate sites. With the first implant 17, the fixing thread 19 has its two free ends 19a, 19b which are fixed to the instrument 16. With the second implant 18, only one free end 20a of the fixing thread 20 is fixed to the slit-film yarn 16, delimiting with the implant 18 a first yarn 21 of the fixing thread 20. Formed between the first yarn 21 and the other yarn 22, which is not fixed to the slit-film yarn 16, is a sliding knot 23. To tense the slit-film yarn 16, the practitioner can exert traction on the free end 22a of the second yarn 22. During this traction the sliding knot 23 moves until it is sufficiently tight and blocks the second yarn 22 on the first yarn 21.

Figure 6:
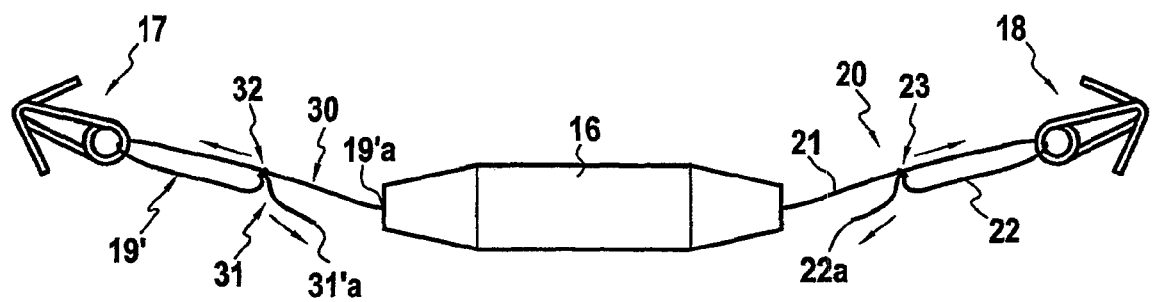

The example illustrated in FIG. 6 differs from that of FIG. 5 in that only one 19'a of the two free ends 19'a, 19'b of the fixing thread 19' of the first implant 17 is fixed to the slit-film yarn 16, thus delimiting with the implant 17 a first fixing yarn 30. Formed between this first yarn 30 and the other yarn 31, not fixed to the slit-film yarn 16, is a sliding knot 32. To tense the slit-film yarn 16, the practitioner exerts traction on the free ends 22a, 31a of the two yarns 22 and 31, which allows a greater possibility of centring the slit-film yarn 16 than in the preceding example.

Figure 7:
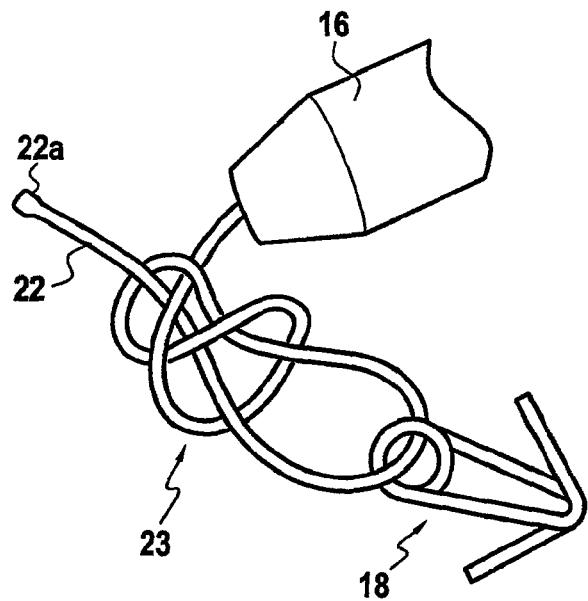
FIG. 7 is an illustration of a sliding knot on a fixing thread as per FIG. 5.

FIG. 7 illustrates an embodiment of a sliding knot 23, of the figure eight loop type, which fully satisfies execution of the embodiments hereinabove, by its capacity to slide and block the two yarns.

The present invention is not limited to the preferred embodiment which has been described hereinabove. The surgical assembly is preferably disposable but the ancillary can optionally be reused after sterilization. The tube with distal cavity which constituted the useful part, described hereinabove, for placing the implant 1 can of course be qualified by a prehension sleeve and be in either a rectilinear or a curved form with the possibility of inclination means allowing placement of the implant blind, its orientable end allowing it to reach spaces not directly accessible.

The invention claimed is:

1. A surgical assembly for implantation of an anchoring and fixing implant comprising:
    at least one fixing thread, and
    an anchoring and fixing surgical implant for implantation into tissue, the implant constituted by a continuous wire with rectilinear portions and curved portions, wherein the implant further comprises:
    a) a central curved portion forming a winding of at least substantially 1.5 turns, and
    b) on either side and in extension of said central portion, a set of two rectilinear portions, specifically an intermediate portion and an end portion, connected to one another by a bent portion at an angle of the order of 30° to 90°, such that the central curved portion is disposed in between the intermediate portions, and
        wherein the rectilinear end portions are oriented divergently so as to make an angle of the order of 60° to 180° between them,
        wherein the intermediate rectilinear portions make an angle of the order of 10° to 30° between them,
        wherein the two bent portions are curved forming and additional two curved portions and the centers of the three curved portions are in the same plane,
        wherein the at least one fixing thread is threaded in the central curved portion of the implant, and
    wherein the intermediate portions extend inwardly in a first direction away from the central curved portion, and the end portions are bent outwardly and downwardly in a second direction that is opposite to the first direction.

2. The implant as claimed in claim 1, wherein the continuous wire is made of shape-memory material such that, in a position of introduction, the two rectilinear end portions can be stressed towards one another, so as to form between them an angle of the order of 10° to 30° and, in an implantation position, resume an initial angular arrangement of the order of 60° to 180°.

3. The implant as claimed in claim 1, wherein the length of the rectilinear end portions is less than the length of the intermediate rectilinear portions.

\* \* \* \* \*

UNITED STATES PATENT AND TRADEMARK OFFICE
CERTIFICATE OF CORRECTION

PATENT NO. : 8,506,595 B2  
APPLICATION NO. : 12/443945  
DATED : August 13, 2013  
INVENTOR(S) : William Houard et al.

Page 1 of 1

It is certified that error appears in the above-identified patent and that said Letters Patent is hereby corrected as shown below:

On the Title page of the Letters Patent, please insert -- (30) Foreign Application Priority Data
Oct. 4, 2006 (FR) ............. 06 08703 --

Signed and Sealed this  
Sixth Day of May, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,506,595 B2
APPLICATION NO. : 12/443945
DATED : August 13, 2013
INVENTOR(S) : Houard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Fifteenth Day of September, 2015

Michelle K. Lee
*Director of the United States Patent and Trademark Office*